US00PP10897P

United States Patent [19]

Faupel

[11] Patent Number: Plant 10,897

[45] Date of Patent: May 11, 1999

[54] AZALEA PLANT NAMED 'PANFILIA'

[75] Inventor: Hans Faupel, Bad Zwischenahn, Germany

[73] Assignee: Landwirtschaftskammer Weser-Ems, Oldenburg, Germany

[21] Appl. No.: 09/005,616

[22] Filed: Jan. 12, 1998

[51] Int. Cl.[6] ..... A01H 5/00

[52] U.S. Cl. ..... Plt./238

[58] Field of Search ..... Plt./238, 239, 240

[56] References Cited

U.S. PATENT DOCUMENTS

P.P. 10,318 4/1998 Baetcke ..... Plt./238

*Primary Examiner*—Howard J. Locker
*Assistant Examiner*—Kent L. Bell
*Attorney, Agent, or Firm*—C. A. Whealy

[57] ABSTRACT

A new and distinct cultivar of Azalea plant named 'Panfilia', characterized by its uniform, upright and outwardly spreading plant habit; freely branching habit; durable dark green leaves; large attractive bicolored double flowers with white to light pink petals with dark pink margins; ruffled flowers; and good postproduction longevity with plants maintaining flowers for about five weeks.

1 Drawing Sheet

The present invention relates to a new and distinct cultivar of Azalea, botanically known as *Rhododendron simsii*, and hereinafter referred to by the cultivar name 'Panfilia'.

The new cultivar was discovered by the inventor in February, 1986, in a controlled environment in Bad Zwischenahn, Germany, as a naturally-occurring mutation of the nonpatented Azalea cultivar 'Georgentor'. The new Azalea was observed as a single plant within a population of flowering plants of the parent cultivar. The selection of this plant was based on its different flower color. Plants of the cultivar 'Georgentor' have light pink flowers whereas plants of the new Azalea have bicolored flowers of white to light pink with dark pink margins.

Asexual reproduction of the new cultivar by terminal cuttings taken at Bad Zwischenahn, Germany, has shown that the unique features of this new Azalea plant are stable and reproduced true to type in successive generations of asexual reproduction.

The following traits have been repeatedly observed and are determined to be the unique characteristics of 'Panfilia'. These characteristics in combination distinguish the new Azalea plant as a new and distinct cultivar:

1. Uniform, upright and outwardly spreading plant habit.
2. Freely branching habit.
3. Durable dark green leaves.
4. Large attractive bicolored double flowers with white to light pink petals with dark pink margins.
5. Ruffled flowers.
6. Good postproduction longevity with plants maintaining flowers for about five weeks.

Plants of the new Azalea can be compared to plants of the bicolored cultivar 'Leopold Astrid' (not patented). However in side-by-side comparisions in Bad Zwischenahn, Germany, under commercial practice, plants of the new Azalea have a darker pink petal margin color, smaller leaves, and shorter peduncles than plants of the cultivar 'Leopold Astrid'.

Plants of the new Azalea can also be compared to plants of the bicolored cultivar 'Sima' (not patented). However in side-by-side comparisions in Bad Zwischenahn, Germany, under commercial practice, plants of the new Azalea have a darker pink petal margin color, fewer petaloids, and fewer flowers per plant than plants of the cultivar 'Sima'.

The new Azalea plant has not been observed under all possible environmental conditions. The phenotype may vary significantly with variations in environment such as temperature, light level, nutrition and water status without, however, any variance in genotype.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of typical plant of 'Panfilia'. Flower and foliage colors in the photograph may appear different from the actual colors due to light reflectance.

DETAILED BOTANICAL DESCRIPTION

The following observations, measurements, values, and comparisons describe plants grown in Salinas, Calif., in 12.5-cm containers under glass with day temperatures ranging from 24 to 27° C., night temperatures ranging from 13 to 16° C., and light levels averaging 4,500 footcandles.

In the following description, color references are made to The Royal Horticultural Society Colour Chart except where general terms of ordinary dictionary significance are used.

Classification:

*Botanical.*—*Rhododendron simsii* cultivar 'Panfilia'.

Parentage: Naturally-occurring mutation of *Rhododendron simsii* cultivar 'Georgentor' (not patented).

Propagation:

*Type.*—By terminal cuttings.

*Time to initiate roots.*—About 30 days at temperatures of 16° C.

*Time to develop roots.*—About 60 days at temperatures of 20° C.

*Rooting habit.*—Fibrous and finely-branched.

Plant description:

*Plant form and growth habit.*—Perennial, evergreen, upright and outwardly spreading, inverted triangle. Moderate vigor.

*Branching habit.*—Dense, freely branching, four to five lateral branches develop after removal of terminal apex.

*Plant height, soil level to top of flowers.*—About 17 cm.

*Plant diameter, area of spread.*—About 28 cm.

*Lateral branch description.*—Length: About 11 cm. Diameter: About 4 mm. Color: Immature: 145A. Mature: 166B, woody. Texture: Pubescent, moderate, brown in color.

Foliage description:

*Arrangement.*—Alternate, single.

*Length.*—About 4.5 cm.

*Width.*—About 2.2 cm.

*Shape.*—Elliptic to oblanceolate.

*Apex.*—Mucronate.

*Base.*—Cuneate.

*Margin.*—Entire.

*Texture.*—Durable, leathery, slight gloss, both surfaces pubescent.

*Color.*—Young foliage, upper surface: 137A. Young foliage, lower surface: 137C. Mature foliage, upper surface: Darker than 147A. Mature foliage, lower surface: 147B.

*Petiole.*—Length: About 9 mm. Diameter: About 2 mm. Color: 138A.

Flower description:

*Natural flowering season.*—Spring after sufficient cool period.

*Flower arrangement.*—Flowers arranged singly at terminals with usually abot five flowers per terminal, occasionally up to ten flowers per terminal. Flowers face outward. Freely flowering.

*Flower appearance.*—Large double flowers. Bicolored, white to light pink with dark pink margins. Petals ruffled at margins. Flowers persistent.

*Flower diameter.*—About 8 cm.

*Flower longevity.*—Six to eight days depending on temperature.

*Flower bud.*—Rate of opening: About two to three days depending on temperatures. Length: About 1.9 cm. Diameter: About 8 mm. Shape: Ovoid. Color: White with dark pink, 63A, edge.

*Petals.*—Appearance: Velvety, smooth. Texture: Glabrous. Arrangement: Double. Outer corolla consists of five fused petals and inner corolla consists of about ten petaloids. Shape: Rounded with rounded apex. Margin: Entire, prominent undulating margins give a ruffled appearance. Length: About 4.75 cm. Width: About 3.5 cm. Color: When opening, upper surface: White, 155D, to light pink, 73D, with dark pink, 63A, margin. When opening, lower surface: White, 155D, to light pink, 73D, with dark pink, 63A, margin. Fully opened, upper surface: White, 155D, to light pink, 73D, with dark pink, 63A, margin. Margin about 5 to 10 mm in width. Flower color does not fade. Fully opened, lower surface: White, 155D, to light pink, 73D, with dark pink, 63A, margin.

*Sepals.*—Appearance: Five sepals fused into a star-shaped calyx. Texture: Very pubescent. Shape: Lanceolate. Apex: Acute. Margin: Entire. Color, outer and inner surfaces: 146B.

*Peduncles.*—Length: About 1.7 cm. Angle: Upright. Strength: Rigid. Color: 145A.

*Reproductive organs.*—Androecium: Stamen number: Five, some may be petaloid. Anther shape: Oblong. Anther size: About 2 mm. Anther color: Dark pink. Amount of pollen: Moderate. Pollen color: Dark orange. Gynoecium: Pistil number: One. Stigma shape: Rounded. Stigma diameter: About 2 mm. Stigma color: Green to dark pink. Style length: About 2.3 cm. Style color: White to light pink. Ovary color: Green.

Disease resistance: No known Azalea diseases observed to date on plants grown under commercial greenhouse conditions.

Seed production: Seed production has not been observed.

It is claimed:

1. A new and distinct Azalea plant named 'Panfilia', as illustrated and described.

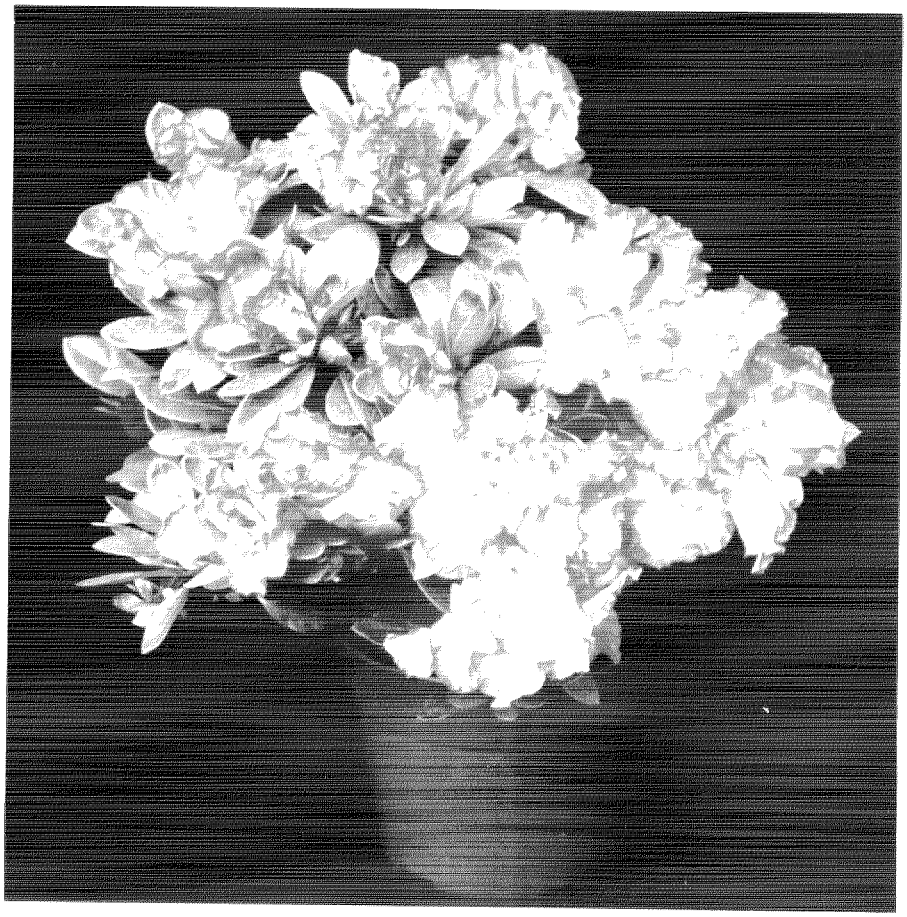

* * * * *